(12) United States Patent
Schmidt

(10) Patent No.: US 9,221,119 B2
(45) Date of Patent: Dec. 29, 2015

(54) HIGH RELIABILITY WIRE WELDING FOR IMPLANTABLE DEVICES

(71) Applicant: ALFRED E. MANN FOUNDATION FOR SCIENTIFIC RESEARCH, Santa Clarita, CA (US)

(72) Inventor: Siegmar Schmidt, Simi Valley, CA (US)

(73) Assignee: ALFRED E. MANN FOUNDATION FOR SCIENTIFIC RESEARCH, Santa Clarita, CA (US)

( * ) Notice: Subject to any disclaimer, the term of this patent is extended or adjusted under 35 U.S.C. 154(b) by 0 days.

(21) Appl. No.: 14/270,115

(22) Filed: May 5, 2014

(65) Prior Publication Data

US 2014/0350651 A1 Nov. 27, 2014

Related U.S. Application Data

(60) Provisional application No. 61/819,459, filed on May 3, 2013.

(51) Int. Cl.
*A61N 1/00* (2006.01)
*B23K 11/00* (2006.01)
*B23K 26/22* (2006.01)
*A61N 1/375* (2006.01)
(Continued)

(52) U.S. Cl.
CPC .......... *B23K 11/0026* (2013.01); *A61N 1/3752* (2013.01); *B23K 11/115* (2013.01); *B23K 26/22* (2013.01); *B23K 28/02* (2013.01); *B23K 2201/32* (2013.01); *Y10T 29/49171* (2015.01)

(58) Field of Classification Search
CPC ... A61N 1/3752; A61N 1/3754; A61N 1/375; B23K 11/0026; B23K 11/115; B23K 2201/32; B23K 26/22; B23K 28/02; Y10T 29/49171
See application file for complete search history.

(56) References Cited

U.S. PATENT DOCUMENTS

| 3,942,535 A | 3/1976 | Schulman et al. |
| 4,082,097 A | 4/1978 | Mann et al. |

(Continued)

FOREIGN PATENT DOCUMENTS

| DE | 102010006837 A1 | 8/2011 |
| EP | 1680182 | 7/2006 |

(Continued)

OTHER PUBLICATIONS

Boiocchi, S., et al., "Self-calibration in high speed current steering CMOS D/A converters", Advanced A-D and D-A Conversion Techniques and Their Applications, 1994, Second International Conference on Cambridge, UK, London, UK, IEE, UK, Jan. 1, 1994, pp. 148-152.

(Continued)

*Primary Examiner* — George Manuel
(74) *Attorney, Agent, or Firm* — Kilpatrick Townsend & Stockton LLP

(57) ABSTRACT

Methods of making an implantable pulse generator are disclosed herein. The implantable pulse generator can include a body defining an internal volume and a plurality of wires extending from out of the internal volume of the body. Some of these wires can be connected, either directly or indirectly to a lead via a welded joint. The welded joint can be created by first resistance welding and then laser welding some of the wires to a connector.

32 Claims, 10 Drawing Sheets

(51) Int. Cl.
   *B23K 11/11*   (2006.01)
   *B23K 28/02*   (2014.01)

(56) References Cited

U.S. PATENT DOCUMENTS

| | | |
|---|---|---|
| 4,468,723 A | 8/1984 | Hughes |
| 4,673,867 A | 6/1987 | Davis |
| 5,143,089 A | 9/1992 | Alt |
| 5,690,693 A | 11/1997 | Wang et al. |
| 5,702,431 A | 12/1997 | Wang et al. |
| 5,735,887 A | 4/1998 | Barreras, Sr. et al. |
| 5,741,316 A | 4/1998 | Chen et al. |
| 5,876,423 A | 3/1999 | Braun |
| 5,877,472 A | 3/1999 | Campbell et al. |
| 6,035,237 A | 3/2000 | Schulman et al. |
| 6,055,456 A | 4/2000 | Gerber |
| 6,057,513 A | 5/2000 | Ushikoshi et al. |
| 6,067,474 A | 5/2000 | Schulman et al. |
| 6,076,017 A | 6/2000 | Taylor et al. |
| 6,164,284 A | 12/2000 | Schulman et al. |
| 6,178,353 B1 | 1/2001 | Griffith et al. |
| 6,185,452 B1 | 2/2001 | Schulman et al. |
| 6,191,365 B1 | 2/2001 | Avellanet |
| 6,208,894 B1 | 3/2001 | Schulman et al. |
| 6,212,431 B1 | 4/2001 | Hahn et al. |
| 6,221,513 B1 | 4/2001 | Lasater |
| 6,246,911 B1 | 6/2001 | Seligman |
| 6,265,789 B1 | 7/2001 | Honda et al. |
| 6,313,779 B1 | 11/2001 | Leung et al. |
| 6,315,721 B2 | 11/2001 | Schulman et al. |
| 6,402,793 B1 * | 6/2002 | Miltich et al. ............... 29/25.03 |
| 6,427,086 B1 | 7/2002 | Fischell et al. |
| 6,438,423 B1 | 8/2002 | Rezai et al. |
| 6,442,434 B1 | 8/2002 | Zarinetchi et al. |
| 6,505,075 B1 | 1/2003 | Weiner |
| 6,516,227 B1 | 2/2003 | Meadows et al. |
| 6,521,350 B2 | 2/2003 | Fey et al. |
| 6,564,807 B1 | 5/2003 | Schulman et al. |
| 6,584,355 B2 | 6/2003 | Stessman |
| 6,600,954 B2 | 7/2003 | Cohen et al. |
| 6,609,032 B1 | 8/2003 | Woods et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,864,755 B2 | 3/2005 | Moore |
| 6,892,098 B2 | 5/2005 | Ayal et al. |
| 6,895,280 B2 | 5/2005 | Meadows et al. |
| 6,901,287 B2 | 5/2005 | Davis et al. |
| 6,986,453 B2 | 1/2006 | Jiang et al. |
| 6,989,200 B2 | 1/2006 | Byers et al. |
| 6,990,376 B2 | 1/2006 | Tanagho et al. |
| 7,051,419 B2 | 5/2006 | Schrom et al. |
| 7,069,081 B2 | 6/2006 | Biggs et al. |
| 7,114,502 B2 | 10/2006 | Schulman et al. |
| 7,127,298 B1 | 10/2006 | He et al. |
| 7,142,925 B1 | 11/2006 | Bhadra et al. |
| 7,177,690 B2 | 2/2007 | Woods et al. |
| 7,191,005 B2 | 3/2007 | Stessman |
| 7,212,110 B1 | 5/2007 | Martin et |
| 7,225,032 B2 | 5/2007 | Schmeling et al. |
| 7,234,853 B2 | 6/2007 | Givoletti |
| 7,245,972 B2 | 7/2007 | Davis |
| 7,286,880 B2 | 10/2007 | Olson et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,328,068 B2 | 2/2008 | Spinelli et al. |
| 7,331,499 B2 | 2/2008 | Jiang et al. |
| 7,369,894 B2 | 5/2008 | Gerber |
| 7,386,348 B2 | 6/2008 | North et al. |
| 7,396,265 B2 | 7/2008 | Darley et al. |
| 7,444,181 B2 | 10/2008 | Shi et al. |
| 7,450,991 B2 | 11/2008 | Smith et al. |
| 7,460,911 B2 | 12/2008 | Cosendai et al. |
| 7,483,752 B2 | 1/2009 | Von Arx et al. |
| 7,496,404 B2 | 2/2009 | Meadows et al. |
| 7,513,257 B2 | 4/2009 | Schulman et al. |
| 7,515,967 B2 | 4/2009 | Phillips et al. |
| 7,532,936 B2 | 5/2009 | Erickson et al. |
| 7,539,538 B2 | 5/2009 | Parramon et al. |
| 7,555,346 B1 | 6/2009 | Woods et al. |
| 7,565,203 B2 | 7/2009 | Greenberg et al. |
| 7,643,880 B2 | 1/2010 | Tanagho et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,965 B2 | 6/2010 | Phillips et al. |
| 7,771,838 B1 | 8/2010 | He et al. |
| 7,774,069 B2 | 8/2010 | Olson et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,904,167 B2 | 3/2011 | Klosterman et al. |
| 7,925,357 B2 | 4/2011 | Phillips et al. |
| 7,932,696 B2 | 4/2011 | Peterson |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,805 B2 | 8/2011 | Swoyer et al. |
| 8,005,549 B2 | 8/2011 | Boser et al. |
| 8,005,550 B2 | 8/2011 | Boser et al. |
| 8,019,423 B2 | 9/2011 | Possover |
| 8,024,047 B2 | 9/2011 | Olson et al. |
| 8,036,756 B2 | 10/2011 | Swoyer et al. |
| 8,044,635 B2 | 10/2011 | Peterson |
| 8,055,337 B2 | 11/2011 | Moffitt et al. |
| 8,103,360 B2 | 1/2012 | Foster |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,175,717 B2 | 5/2012 | Haller et al. |
| 8,180,452 B2 | 5/2012 | Shaquer |
| 8,214,042 B2 | 7/2012 | Ozawa et al. |
| 8,219,196 B2 | 7/2012 | Torgerson |
| 8,219,202 B2 | 7/2012 | Giftakis et al. |
| 8,255,057 B2 | 8/2012 | Fang et al. |
| 8,314,594 B2 | 11/2012 | Scott et al. |
| 8,332,040 B1 | 12/2012 | Winstrom |
| 8,362,742 B2 | 1/2013 | Kallmyer |
| 8,369,943 B2 | 2/2013 | Shuros et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,515,545 B2 | 8/2013 | Trier |
| 8,538,530 B1 | 9/2013 | Orinski |
| 8,549,015 B2 | 10/2013 | Barolat |
| 8,554,322 B2 | 10/2013 | Olson et al. |
| 8,555,894 B2 | 10/2013 | Schulman et al. |
| 8,577,474 B2 | 11/2013 | Rahman et al. |
| 8,588,917 B2 | 11/2013 | Whitehurst et al. |
| 8,700,175 B2 | 4/2014 | Fell |
| 8,750,985 B2 | 6/2014 | Parramon et al. |
| 2002/0116042 A1 | 8/2002 | Boling |
| 2003/0078633 A1 | 4/2003 | Firlik et al. |
| 2004/0106963 A1 | 6/2004 | Tsukamoto et al. |
| 2005/0104577 A1 | 5/2005 | Matei et al. |
| 2006/0016452 A1 | 1/2006 | Goetz et al. |
| 2006/0050539 A1 | 3/2006 | Yang et al. |
| 2006/0142822 A1 | 6/2006 | Tulgar |
| 2006/0206166 A1 | 9/2006 | Weiner |
| 2007/0073357 A1 | 3/2007 | Rooney et al. |
| 2007/0293914 A1 | 12/2007 | Woods et al. |
| 2008/0132961 A1 | 6/2008 | Jaax et al. |
| 2008/0172109 A1 | 7/2008 | Rahman et al. |

(56) References Cited

U.S. PATENT DOCUMENTS

| | | |
|---|---|---|
| 2009/0088816 A1 | 4/2009 | Harel et al. |
| 2009/0105785 A1 | 4/2009 | Wei et al. |
| 2009/0112291 A1 | 4/2009 | Wahlstrand et al. |
| 2009/0259273 A1 | 10/2009 | Figueiredo et al. |
| 2010/0076534 A1 | 3/2010 | Mock |
| 2011/0152959 A1 | 6/2011 | Sherwood et al. |
| 2011/0270269 A1 | 11/2011 | Swoyer et al. |
| 2011/0278948 A1 | 11/2011 | Forsell |
| 2011/0301667 A1 | 12/2011 | Olson et al. |
| 2012/0016447 A1 | 1/2012 | Zhu et al. |
| 2012/0041512 A1 | 2/2012 | Weiner |
| 2012/0046712 A1 | 2/2012 | Woods et al. |
| 2012/0071950 A1 | 3/2012 | Archer |
| 2012/0119698 A1 | 5/2012 | Karalis et al. |
| 2012/0130448 A1 | 5/2012 | Woods et al. |
| 2012/0259381 A1 | 10/2012 | Smith et al. |
| 2012/0262108 A1 | 10/2012 | Olson et al. |
| 2012/0274270 A1 | 11/2012 | Dinsmoor et al. |
| 2013/0023958 A1 | 1/2013 | Fell |
| 2013/0096651 A1 | 4/2013 | Ozawa et al. |
| 2013/0150925 A1 | 6/2013 | Vamos et al. |
| 2013/0211479 A1 | 8/2013 | Olson et al. |
| 2013/0303942 A1 | 11/2013 | Damaser et al. |

FOREIGN PATENT DOCUMENTS

| | | |
|---|---|---|
| EP | 1904153 | 4/2008 |
| EP | 2243509 | 10/2010 |
| JP | 2003047179 A | 2/2003 |
| WO | WO 00-66221 A1 | 11/2000 |
| WO | WO 02/03408 A2 | 1/2002 |
| WO | WO 2004-103465 A1 | 12/2004 |
| WO | WO 2008/021524 | 2/2008 |
| WO | WO 2009-051539 A1 | 4/2009 |
| WO | WO 2009-091267 A2 | 7/2009 |
| WO | WO 2010-042056 A1 | 4/2010 |
| WO | WO 2010-042057 A1 | 4/2010 |
| WO | WO 2011/059565 | 5/2011 |
| WO | WO 2013/141884 | 9/2013 |

OTHER PUBLICATIONS

Gundason, G., "A low-power ASK demodulator for Inductively coupled implantable electronics", Solid-State Circuits Conference, 2000, Esscirc 00, Proceedings of the 26RD European, IEEE, Sep. 19, 2000, pp. 385-388.

Humayun, M.S., et al., "A Variable Range Bi-Phasic Current Stimulus Driver Circuitry for an Implantable Retinal Prosthetic Device", IEEE Journal of Solid-State Circuits, IEEE Service Center, Piscataway, NJ, USA, vol. 40, No. 3, Mar. 1, 2005, pp. 763-771.

Van Paemel, M., "High-Efficiency Transmission for Medical Implants", IEEE Solid-State Circuits Magazine, IEEE, USA, vol. 3, No. 1, Jan. 1, 2011, pp. 47-59.

Wang, Chua-Chin, et al., "A 140-dB CMRR Low-noise Instrumentation Amplifier for Neural Signal Sensing", Circutis and Systems, 2006, APCCAS 2006, IEEE Asia Pacific Conference on IEEE, Piscataway, NJ, USA, Dec. 1, 2006, pp. 696-699.

* cited by examiner

HIGH RELIABILITY WIRE WELDING FOR IMPLANTABLE DEVICES

CROSS-REFERENCES TO RELATED APPLICATIONS

This application claims the benefit of U.S. Provisional Application No. 61/819,459, entitled "HIGH RELIABILITY WIRE WELDING FOR IMPLANTABLE DEVICES," and filed on May 3, 2013, the entirety of which is hereby incorporated by reference herein.

BACKGROUND OF THE INVENTION

Some medical devices such as some implantable pulse generators and other electronic devices have become smaller over time. There are benefits to minimizing the size of these implanted devices, such as increased implantability throughout the body, shortened recovery time after implantation, and fewer complications arising from the implantation. However, the smaller size of these devices also poses challenges. For instance, electrical connections between the various components, sub-components and other elements of the implantable device and/or associated devices or accessories may often need to be made in small areas and volumes. These small areas and volumes can sometimes have constrained access and/or visibility. However, in spite of the difficulties in making these connections in small volumes, the connections may need to be robust and durable.

BRIEF SUMMARY OF THE INVENTION

One aspect of the present disclosure relates to a method of connecting leads to an implantable pulse generator. In some embodiments, the implantable pulse generator can include: a biocompatible housing, a plurality of biocompatible wires extending from the biocompatible housing, which biocompatible wires can include a longitudinal axis, and a feedthrough. In some embodiments, the feedthrough and the biocompatible housing together define a sealed volume, and in some embodiments, the biocompatible wires extend through the feedthrough. The method includes positioning one of the biocompatible wires and a connecting piece such that the one of the biocompatible wires and the connecting piece contact, resistance welding one of the biocompatible wires and the connecting piece together, and energy beam welding the one of the biocompatible wires and the connecting piece together.

In some embodiments, the one of the biocompatible wires and the connecting pieces are positioned to create a lap-joint. In some embodiments of the method, energy beam welding can be laser welding. In some embodiments, energy beam welding the biocompatible wire can include: aiming an energy beam at an edge of the one of the biocompatible wires such that a portion of the energy beam is tangent to the edge, and welding the edge of the one of the biocompatible wires to the connecting piece.

In some embodiments of the method, the heat affected zone created by welding the edge of the one of the biocompatible wires to the connecting piece extends from the edge of the one of the biocompatible wires. In some embodiments, the heat affected zone created by welding the edge of the one of the biocompatible wires to the connecting pieces extends to a second edge of the one of the biocompatible wires. In one exemplary embodiment, the method includes enclosing the welds of the one of the biocompatible wires and the connecting piece in a non-conductive material, and in one embodiment, the non-conductive material can be a reacted resin.

In some embodiments of the method, the connecting piece can include a second biocompatible wire that can have a longitudinal axis. In some embodiments, the positioning the one of the biocompatible wires and the connecting piece that is the second biocompatible wire includes overlapping a portion of both the one of the biocompatible wires and the second biocompatible wire such that the longitudinal axes of the biocompatible wire and the second biocompatible wire are non-parallel. In some embodiments, the angle between the longitudinal axes of the biocompatible wire and the second biocompatible wire is between 30 and 150 degrees.

In some embodiments, the connecting piece can include at least one connector. In one exemplary embodiment, the connecting piece can be a first connector and a second connector. In some embodiments, a first group of the biocompatible wires connect to the first connector and a second group of biocompatible wires extend past the first connector and connect to the second connector. In some embodiments, the method includes creating an insulative barrier between the second group of wires and the first connector before welding the second group of wires to the second connector. In some embodiments, resistance welding can include contacting at least one of the biocompatible wires and the connecting piece with at least one electrode of an resistance welder. In some embodiments, the wires can have a diameter between 0.05 mm and 0.5 mm.

One aspect of the present disclosure relates to an implantable pulse generator. The implantable pulse generator includes a biocompatible housing, and a plurality of biocompatible wires extending from the biocompatible housing. In some embodiments, each of the biocompatible wires can have a longitudinal axis. The implantable pulse generator can include a feedthrough. In some embodiments, the feedthrough and the biocompatible housing together define a sealed volume. In one exemplary embodiment, the biocompatible wires extend through the feedthrough. The implantable pulse generator can include a conductive connecting piece welded to one of the biocompatible wires. In some embodiments, the conductive connecting piece is joined to one of the biocompatible wires at a joint via a first weld and a second weld. In some embodiments, the second weld is offset from the longitudinal axis of the one of the biocompatible wire or at the end of the biocompatible wire.

In some embodiments of the implantable pulse generator, the plurality of biocompatible wires can be made from a platinum-iridium alloy. In some embodiments, the joint of the one of the biocompatible wires and the conductive connecting piece can be a lap joint. Some embodiments of the implantable pulse generator include a cap enclosing the biocompatible wires and the joint of the one of the biocompatible wires and the connecting piece. In some embodiments, the cap is non-conductive, and in some embodiments, the cap is permeable to body fluids. In some embodiments, the cap can be a reacted resin In some embodiments of the implantable pulse generator, the connecting piece can be a second biocompatible wire having a longitudinal axis. In some embodiments, at the first weld of the joint, the longitudinal axis of the one of the biocompatible wires is non-parallel with the longitudinal axis of the second biocompatible wire.

In some embodiments, the connecting piece can include at least one connector. In some embodiments, the connecting piece can be a first connector and a second connector. In some embodiments, a first group of the biocompatible wires connect to the first connector and a second group of biocompatible wires extend past the first connector and connect to the second connector.

One aspect of the present disclosure relates to a method of connecting leads to an implantable pulse generator. In some embodiments, the implantable pulse generator can include: a biocompatible housing, an array of biocompatible wires extending from the biocompatible housing, each of which biocompatible wires can have a longitudinal axis, and a feedthrough. In some embodiments, the feedthrough and the biocompatible housing together define a sealed volume. In some embodiments, the biocompatible wires extend through the feedthrough. The method can include resistance welding each of the biocompatible wires of the array of biocompatible wires to a connecting piece and energy beam welding each of the biocompatible wires of the array of biocompatible wires to a connecting piece.

In some embodiments, the connecting piece can be a plurality of second wires. In some embodiments, each of the biocompatible wires of the array of biocompatible wires is connected to a unique one of the second wires. In some embodiments, the connecting piece can be a connector having a plurality of contacts. In some embodiments, each of the biocompatible wires of the array of biocompatible wires is connected to a unique one of the plurality of contacts. In some embodiments, resistance welding can include contacting at least one of the biocompatible wires and connecting piece with at least one electrode of an resistance welder. In some embodiments, the wires have a diameter between 0.05 mm and 0.5 mm.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

Figure 1:
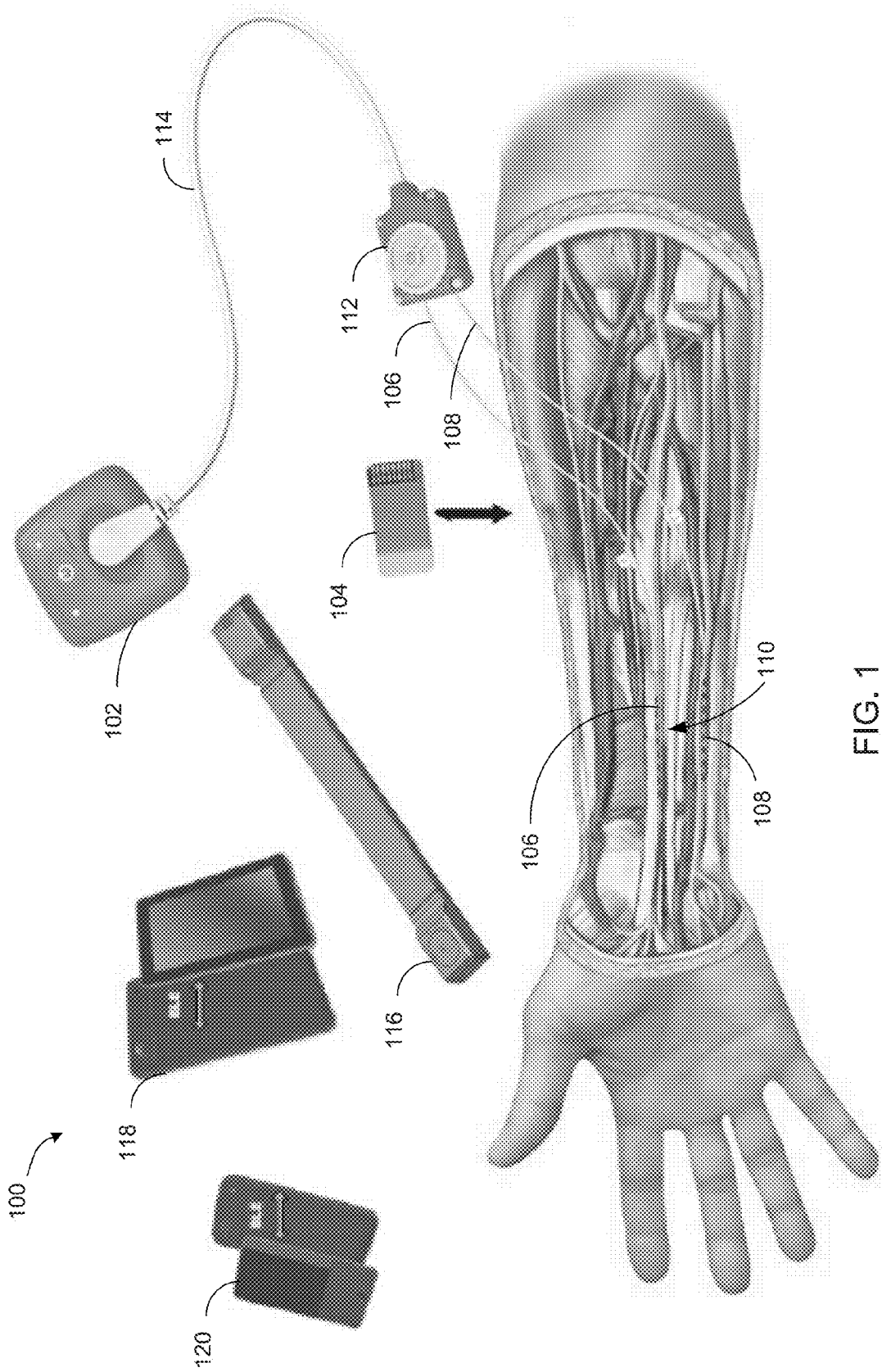
FIG. 1 is a schematic illustration of one embodiment of an implantable neurostimulation system.

In the appended figures, similar components and/or features may have the same reference label. Where the reference label is used in the specification, the description is applicable to any one of the similar components having the same reference label.

DETAILED DESCRIPTION OF THE INVENTION

Some of the embodiments described below are described in the context of components of a neurostimulation system for treating neuropathic pain. A significant percentage of the Western (EU and US) population is affected by Neuropathic pain (chronic intractable pain due to nerve damage). In many people, this pain is severe. There are thousands of patients that have chronic intractable pain involving a nerve. Neuropathic pain can be very difficult to treat with only half of patients achieving partial relief. Thus, determining the best treatment for individual patients remains challenging. Conventional treatments include certain antidepressants, antiepileptic drugs and opioids. However, side effects from these drugs can be detrimental. In some of these cases, electrical stimulation, including FES, can provide effect treatment of this pain without the drug-related side effects.

A spinal cord stimulator is a device used to deliver pulsed electrical signals to the spinal cord to control chronic pain. Because electrical stimulation is a purely electrical treatment and does not cause side effects similar to those caused by drugs, an increasing number of physicians and patients favor the use of electrical stimulation over drugs as a treatment for pain. The exact mechanisms of pain relief by spinal cord stimulation (SCS) are unknown. Early SCS trials were based the Gate Control Theory, which posits that pain is transmitted by two kinds of afferent nerve fibers. One is the larger myelinated Aδ fiber, which carries quick, intense-pain messages. The other is the smaller, unmyelinated "C" fiber, which transmits throbbing, chronic pain messages. A third type of nerve fiber, called Aβ, is "non-nociceptive," meaning it does not transmit pain stimuli. The gate control theory asserts that signals transmitted by the Aδ and C pain fibers can be thwarted by the activation/stimulation of the non-nociceptive Aβ fibers and thus inhibit an individual's perception of pain. Thus, neurostimulation provides pain relief by blocking the pain messages before they reach the brain.

SCS is often used in the treatment of failed back surgery syndrome, a chronic pain syndrome that has refractory pain due to ischemia. SCS complications have been reported in a large portion, possibly 30% to 40%, of all SCS patients. This increases the overall costs of patient pain management and decreases the efficacy of SCS. Common complications include: infection, hemorrhaging, injury of nerve tissue, placing device into the wrong compartment, hardware malfunction, lead migration, lead breakage, lead disconnection, lead erosion, pain at the implant site, generator overheating, and charger overheating. The occurrence rates of common complications are surprisingly high: including lead extension connection issues, lead breakage, lead migration and infection.

Peripheral neuropathy, another condition that can be treated with electrical stimulation, may be either inherited or acquired. Causes of acquired peripheral neuropathy include physical injury (trauma) to a nerve, viruses, tumors, toxins, autoimmune responses, nutritional deficiencies, alcoholism, diabetes, and vascular and metabolic disorders. Acquired peripheral neuropathies are grouped into three broad categories: those caused by systemic disease, those caused by trauma, and those caused by infections or autoimmune disorders affecting nerve tissue. One example of an acquired peripheral neuropathy is trigeminal neuralgia, in which damage to the trigeminal nerve (the large nerve of the head and face) causes episodic attacks of excruciating, lightning-like pain on one side of the face.

A high percentage of patients with peripheral neuropathic pain do not benefit from SCS for various reasons. However, many of these patients can receive acceptable levels of pain relief via direct electrical stimulation to the corresponding peripheral nerves. This therapy is called peripheral nerve stimulation (PNS). As FDA approved PNS devices have not been commercially available in the US market, Standard spinal cord stimulator (SCS) devices are often used off label by pain physicians to treat this condition. A significant portion of SCS devices that have been sold may have been used off-label for PNS.

As current commercially-available SCS systems were designed for stimulating the spinal cord and not for peripheral nerve stimulation, there are more device complications associated with the use of SCS systems for PNS than for SCS. Current SCS devices (generators) are large and bulky. In the event that an SCS is used for PNS, the SCS generator is typically implanted in the abdominal or in the lower back above the buttocks and long leads are tunneled across multiple joints to reach the target peripheral nerves in the arms, legs or face. The excessive tunneling and the crossing of joints leads to increased post-surgical pain and higher device failure rates. Additionally, rigid leads can lead to skin erosion and penetration, with lead failure rates being far too high within the first few years of implantation. Many or even most complications result in replacement surgery and even multiple replacement surgeries in some cases.

One example of an implantable neurostimulation system 100 is shown in FIG. 1, which implantable neurostimulation system 100 can be, for example, a peripherally-implantable neurostimulation system 100. In some embodiments, the implantable neurostimulation system 100 can be used in treating patients with, for example, chronic, severe, refractory neuropathic pain originating from peripheral nerves. In some embodiments, the implantable neurostimulation system 100 can be used to either stimulate a target peripheral nerve or the posterior epidural space of the spine.

The implantable neurostimulation system 100 can include one or several pulse generators. The pulse generators can comprise a variety of shapes and sizes, and can be made from a variety of materials. In some embodiments, the one or several pulse generators can generate one or several non-ablative electrical pulses that are delivered to a nerve to control pain. In some embodiments, these pulses can have a pulse amplitude of between 0-100,000 mA, 0-10,000 mA, 0-1,000 mA, 0-100 mA, 0-50 mA, 0-25 mA, and/or any other or intermediate range of amplitudes. One or more of the pulse generators can include a processor and/or memory. In some embodiments, the processor can provide instructions to and receive information from the other components of the implantable neurostimulation system 100. The processor can act according to stored instructions, which stored instructions can be located in memory, associated with the processor, and/or in other components of the content injection system 100. The processor can, in accordance with stored instructions, make decisions. The processor can comprise a microprocessor, such as a microprocessor from Intel® or Advanced Micro Devices, Inc.®, or the like.

In some embodiments, the stored instructions directing the operation of the processor may be implemented by hardware, software, scripting languages, firmware, middleware, microcode, hardware description languages, and/or any combination thereof When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

In some embodiments, the memory of one or both of the pulse generators can be the storage medium containing the stored instructions. The memory may represent one or more memories for storing data, including read only memory (ROM), random access memory (RAM), magnetic RAM, core memory, magnetic disk storage mediums, optical storage mediums, flash memory devices and/or other machine readable mediums for storing information. In some embodiments, the memory may be implemented within the processor or external to the processor. In some embodiments, the memory can be any type of long term, short term, volatile, nonvolatile, or other storage medium and is not to be limited to any particular type of memory or number of memories, or type of media upon which memory is stored. In some embodiments, the memory can include, for example, one or both of volatile and nonvolatile memory. In one specific embodiment, the memory can include a volatile portion such as RAM memory, and a nonvolatile portion such as flash memory.

In some embodiments, one of the pulse generators can be an external pulse generator 102 or an implantable pulse generator 104. The external pulse generator 102 can be used to evaluate the suitability of a patient for treatment with the implantable neurostimulation system 100 and/or for implantation of an implantable pulse generator 104.

In some embodiments, one of the pulse generators can be the implantable pulse generator 104, which can be sized and shaped, and made of material to allow implantation of the implantable pulse generator 104 inside of a body. In some embodiments, the implantable pulse generator 104 can be sized and shaped so as to allow placement of the implantable pulse generator 104 at any desired location in a body, and in some embodiments, placed proximate to a peripheral nerve such that leads (discussed below) are not tunneled across joints and/or such that extension cables are not needed.

In some embodiments, the electrical pulses generated by the pulse generator can be delivered to one or several nerves 110 and/or to tissue proximate to one or several nerves 110 via one or several leads. The leads can include conductive portions, such as electrodes or contact portions of electrodes, and non-conductive portions. The leads can have a variety of shapes, can be in a variety of sizes, and can be made from a variety of materials, which size, shape, and materials can be dictated by the application or other factors.

In some embodiments, the leads can include an anodic lead 106 and/or a cathodic lead 108. In some embodiments, the anodic lead 106 and the cathodic lead 108 can be identical leads, but can receive pulses of different polarity from the pulse generator.

In some embodiments, the leads can connect directly to the pulse generator, and in some embodiments, the leads can be connected to the pulse generator via a connector 112 and a connector cable 114. The connector 112 can comprise any device that is able to electrically connect the leads to the connector cable 114. Likewise, the connector cable can be any device capable of transmitting distinct electrical pulses to the anodic lead 106 and the cathodic lead 108.

In some embodiments, the implantable neurostimulation system 100 can include a charger 116 that can be configured to recharge the implantable pulse generator 104 when the implantable pulse generator 104 is implanted within a body. The charger 116 can comprise a variety of shapes, sizes, and features, and can be made from a variety of materials. Like the pulse generators 102, 104, the charger 116 can include a processor and/or memory having similar characteristics to those discussed above. In some embodiments, the charger 116 can recharge the implantable pulse generator 104 via an inductive coupling.

In some embodiments, one or several properties of the electrical pulses can be controlled via a controller. In some embodiments, these properties can include, for example, the frequency, strength, pattern, duration, or other aspects of the timing and magnitude of the electrical pulses. In one embodiment, these properties can include, for example, a voltage, a current, or the like. In one embodiment, a first electrical pulse can have a first property and a second electrical pulse can have a second property. This control of the electrical pulses can include the creation of one or several electrical pulse programs, plans, or patterns, and in some embodiments, this can include the selection of one or several pre-existing electrical pulse programs, plans, or patterns. In the embodiment depicted in FIG. 1, the implantable neurostimulation system 100 includes a controller that is a clinician programmer 118. The clinician programmer 118 can be used to create one or several pulse programs, plans, or patterns and/or to select one or several of the created pulse programs, plans, or patterns. In some embodiments, the clinician programmer 118 can be used to program the operation of the pulse generators including, for example, one or both of the external pulse generator 102 and the implantable pulse generator 104. The clinician programmer 118 can comprise a computing device that can wiredly and/or wirelessly communicate with the pulse generators. In some embodiments, the clinician programmer 118 can be further configured to receive information from the pulse generators indicative of the operation and/or effectiveness of the pulse generators and the leads.

In some embodiments, the controller of the implantable neurostimulation system 100 can include a patient remote 120. The patient remote 120 can comprise a computing device that can communicate with the pulse generators via a wired or wireless connection. The patient remote 120 can be used to program the pulse generator, and in some embodiments, the patient remote 120 can include one or several pulse generation programs, plans, or patterns created by the clinician programmer 118. In some embodiments, the patient remote 120 can be used to select one or several of the pre-existing pulse generation programs, plans, or patterns and to select, for example, the duration of the selected one of the one or several pulse generation programs, plans, or patterns.

Advantageously, the above outlined components of the implantable neurostimulation system 100 can be used to control and provide the generation of electrical pulses to mitigate patient pain.

Figure 2:
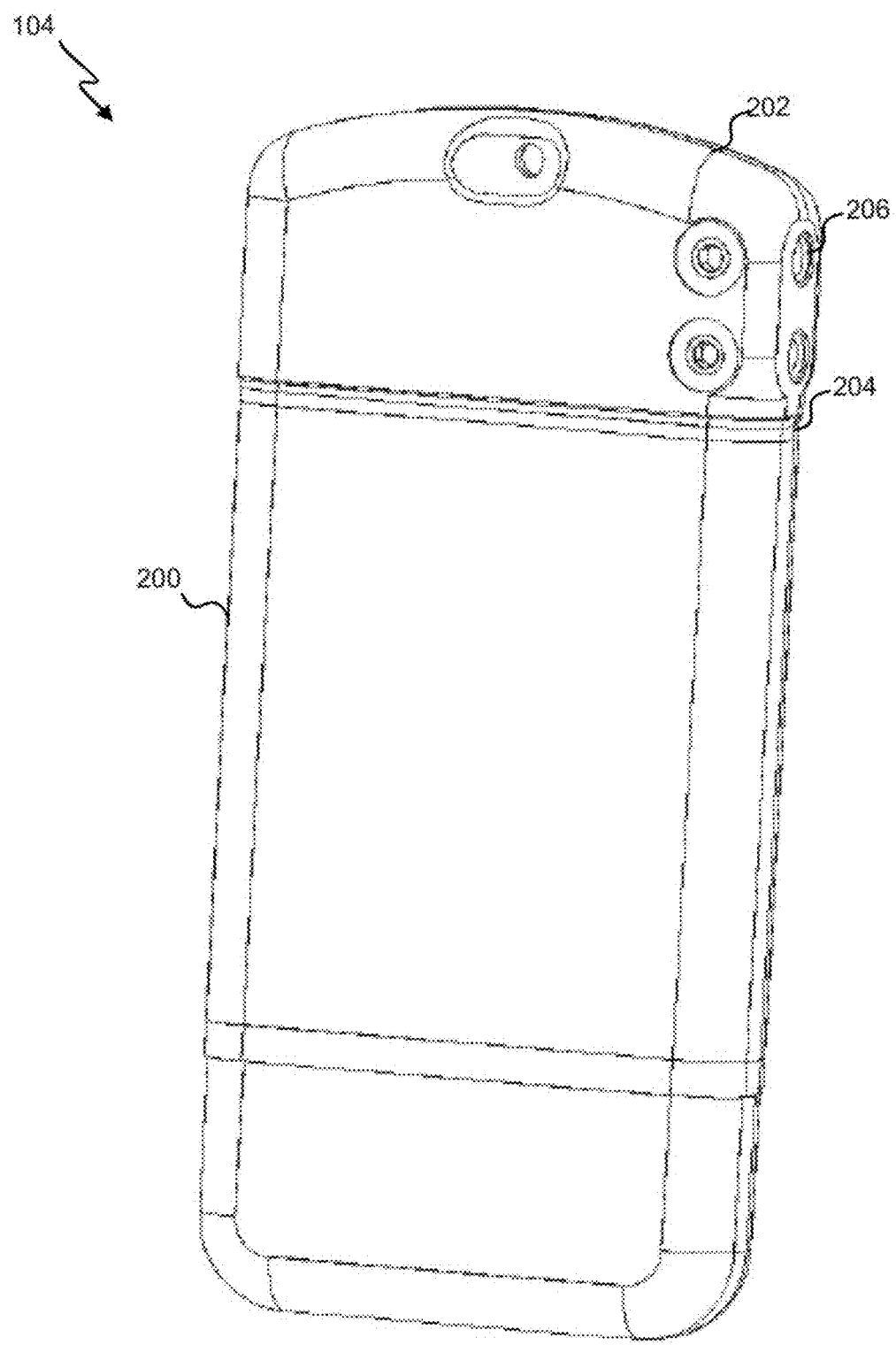
FIG. 2 is a perspective view of one embodiment of an implantable pulse generator (IPG).

With reference now to FIG. 2, a perspective view of one embodiment of the implantable pulse generator (IPG) 104 is shown. The implantable pulse generator 104 can include a body 200 or a housing. The body 200 may be configured to be hermetically sealed or sealable (e.g. such that the interior of the body 200 is hermetically isolated from the surrounding environment outside of the body 200). The body 200 can, together with other components of the implantable pulse generator 104, define an internal volume of the implantable pulse generator 104. In some embodiments, this internal volume of the implantable pulse generator 104 can contain, for example, one or several energy storage devices such as, for example, one or several batteries or rechargeable batteries, one or several processors having features similar to those discussed above, and/or memory. In some embodiments, the body 200 of the implantable pulse generator 104 can comprise a biocompatible material such as, for example, a biocompatible metal. In one specific embodiment, the body 200 of the implantable pulse generator 104 can be titanium.

The implantable pulse generator 104 can include a cap 202. In some embodiments, the cap 202 can cover and/or protect one or several components of the implantable pulse generator 104. The cap 202 can be sized and shaped according to the one or several components of the implantable pulse generator that are covered and/or protected by the cap 202. In some embodiments, the cap 202 can cover one or several wires, connectors, joints, or the like. The cap 202 can comprise a biocompatible material that can be permeable and/or impermeable to body fluids. In some embodiments, for example, the cap 202 can comprise a polymer, a composite, a reactive resin such as, for example, and epoxy, or the like. In some instances, while the cap 202 may provide some protection for the wires, connectors, joints, or other elements housed within the cap 202, the space inside the cap 202 is not hermetically sealed or sealable relative to the environment outside of the cap 202.

Figure 3:
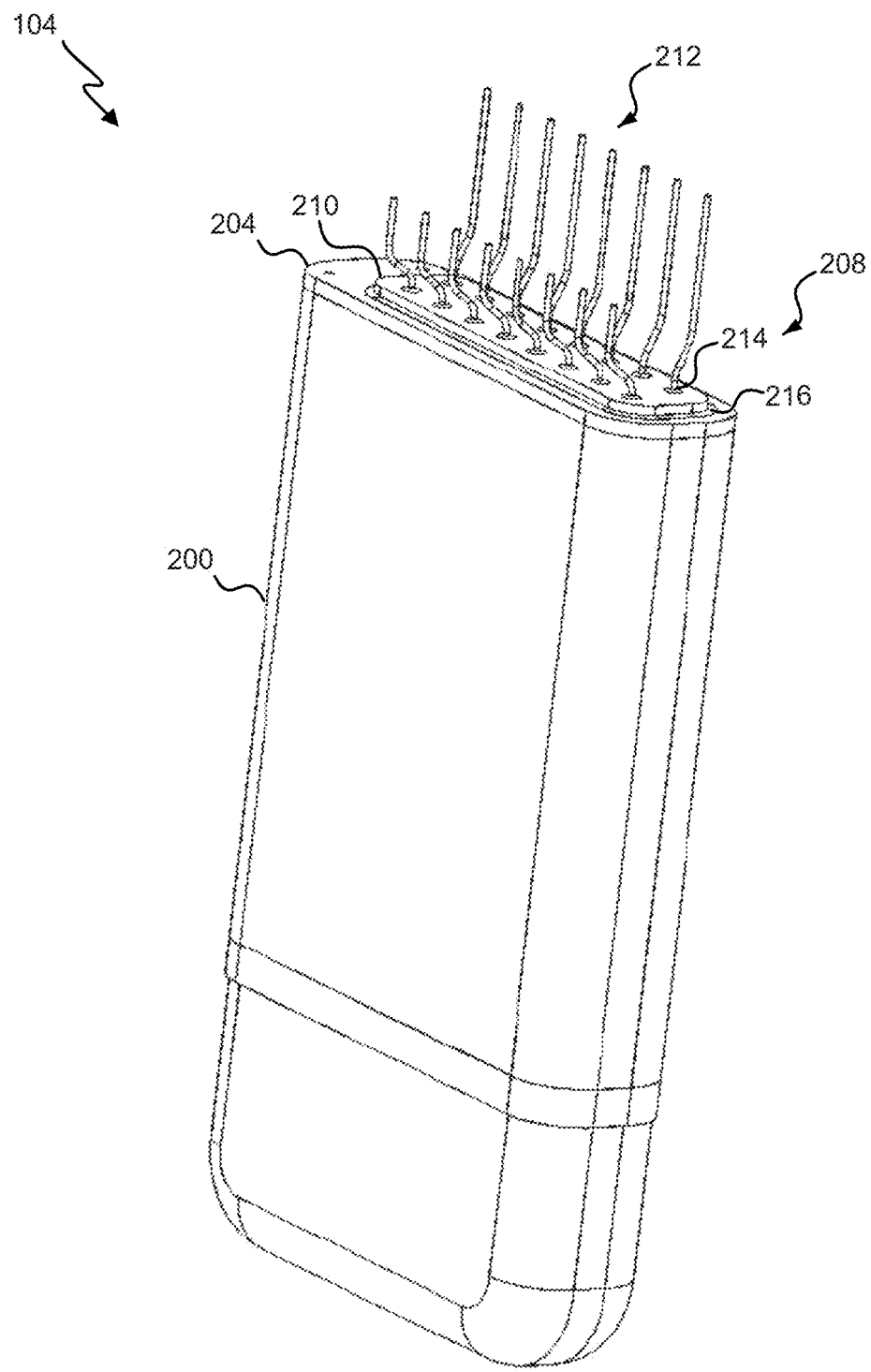
FIG. 3 is a perspective view of the connection wires of the implantable pulse generator.

In the embodiment depicted in the figures, the cap 202 is connected to the body 200 of the implantable pulse generator 104 via the feedthrough plate 204 shown in FIG. 3. In some embodiments, the feedthrough plate 204 can, in connection with the body 200 define the internal volume of the implantable pulse generator. In some embodiments, the feedthrough plate 204 can be sealingly connected to the body 200 such as, for example, via one or several: welds or welded joints, mechanical connectors, and/or the like. In some embodiments, the feedthrough plate 204 can be sized and shaped such that the perimeter of the feedthrough plate 204 matches the perimeter of one or both of the cap 202 and the body 200.

The implantable pulse generator 104 can include one or several connector receptacles 206 as shown in FIG. 2. In some embodiments, the one or several connector receptacles 206 can be configured to allow detachable connection to, for example, leads 106, 108 and/or connector cable 114. In some embodiments, the connector receptacle 206 can include one or several features configured to engage and/or electrically connect with the leads 106, 108 and/or the connector cable 114. In some embodiments, the connector receptacles 206 can be accessible through the cap 202.

With reference now to FIG. 3 a perspective view of one embodiment of the feedthrough assembly 208 and the connection wires 212 of the implantable pulse generator 104 is shown. In some embodiments, the feedthrough assembly 208 can include one or several features configured to cooperate with the body 200 to hermetically seal and define the internal volume of the implantable pulse generator 104. The feedthrough assembly 208 can include the feedthrough plate 204 discussed above and a feedthrough core 210. The feedthrough core 210 can comprise a variety of shapes and sizes and can be made from a variety of materials. In some embodiments, the feedthrough core 214 can be made from an insulative and/or biocompatible material, and in some embodiments, the feedthrough core 214 can comprise, for example, a polymer, a composite, and/or a ceramic material. In some instances, the feedthrough core 214 can be several separate or distinct feedthrough cores (e.g. a separate and distinct feedthrough core for each wire passing through the feedthrough, as opposed to a single feedthrough core 214 for several wires, as shown in FIG. 3).

In some embodiments, the feedthrough core 210 can include a plurality of holes 214 through which the connector wires 212 can extend. In some embodiments, the plurality of holes 214 can extend from the internal volume of the body 202 outside of the internal volume of the body 200. The plurality of holes 214 can be sized and shaped according to the size and shape of the connector wires 212 to allow one or several of the connector wires 212 to pass through each of the plurality of holes 214. In some embodiments, the plurality of holes 214 can be sized and shaped according to the size and shape of the connector wires 212 to allow one or several of the connector wires 212 to pass through each of the plurality of holes 214 without compromising the hermetic seal of the feedthrough core 210. In some embodiments, the holes 214 through which the wires 212 pass can be sealed. In some embodiments, the sealing of the holes 214 through which the wires 212 pass can advantageously allow the sealing and/or the hermetic sealing of the internal volume of the body 200. In some embodiments, the holes 214 can be sealed with the seal that can be, for example, a braze joint connecting the feedthrough core to the wires 212. In some embodiments, the braze joint can be, for example, a gold brazed joint.

The feedthrough core 210 can be sealingly connected to the feedthrough plate 204 via seal 216. The sealing of the feedthrough core 210 to the feedthrough plate 204 can facilitate the sealing and/or the hermetic sealing of the internal volume of the body 200. The hermetic sealing and/or sealing of the internal volume of the body can protect the one or several components of the implantable pulse generator 104 located within the internal volume of the body 200. In some embodiments, the seal 216 can be biocompatible. In some embodiments, the seal 216 can be a brazed joint connecting to the feedthrough plate 204 and the feedthrough core 210. In some embodiments, the brazed joint can be, for example, a gold brazed joint.

As seen in FIG. 3, wires 212 extend through the holes 214 in the feedthrough core 210. In some embodiments, the wires 212 can connect to one or several of the components of the implantable pulse generator 104, which components are contained in the internal volume of the body 200. In some embodiments, the wires 212 can deliver one or several electrical pulses from the components contained in the internal volume of the body 200 to the leads 106, 108 and/or the connector cable 114.

The wires 212 can be made from a variety of materials. In some embodiments, the wires 212 can be biocompatible and can be, for example, a platinum-iridium alloy. In some embodiments, the platinum-iridium alloy of the wires 212 can be between 60% and 100% platinum, between 70% and 95% platinum, between 80% and 90% platinum, approximately 80% platinum, approximately 90% platinum, and/or any other or intermediate percent platinum. In some embodiments, the platinum-iridium alloy of the wires 212 can be between 40% and 0% iridium, between 30% and 5% iridium, between 20% and 10% iridium, approximately 20% iridium, approximately 10% iridium, and/or any other or intermediate percent iridium. In some embodiments, and as used herein, approximately defines a range of 20%, 10%, 5%, or 1% of the value that approximately modifies.

The wires 212 can comprise a variety of shapes and sizes. In some embodiments, the shapes and sizes wires 212 can be selected based on expected or expected maximum currents passing through the wires 212, costs, and implant ability considerations. In some embodiments, the wires 212 can be cylindrical and can have a diameter of, for example, between 0.001 mm and 5 mm, between 0.01 mm and 1 mm, between 0.05 mm and 0.5 mm, between 0.1 mm and 0.3 mm, approximately 0.2 mm, and/or any other or intermediate diameter or range of diameters. In some embodiments, the wires 212 can have a length such that the wires 212 extend through the feedthrough assembly 208 and out of the internal volume of the body 200, in other words, the wires 212 can have a length such that the wires 212 extend beyond an outer surface of the feedthrough assembly 208. In some embodiments, the length of the extension of one or several of the wires 212 beyond the outer surface of the feedthrough assembly 208 can be between 0.1 cm and 10 cm, between 0.5 cm and 5 cm, approximately 3 cm, approximately 2 cm, proximally 1 cm, and/or any other or intermediate length beyond the outer surface of the feedthrough assembly 208.

In some embodiments, one or several of the wires 212 can be connected to a connecting piece. In some embodiments, the connecting piece can include, for example, another wire, a connector, a connector receptacle, or the like. The details of how one or several of the wires 212 are connected to the connecting piece are discussed below, with one embodiment referencing FIGS. 4-6 and another embodiment referencing FIGS. 8-10.

Figure 4:
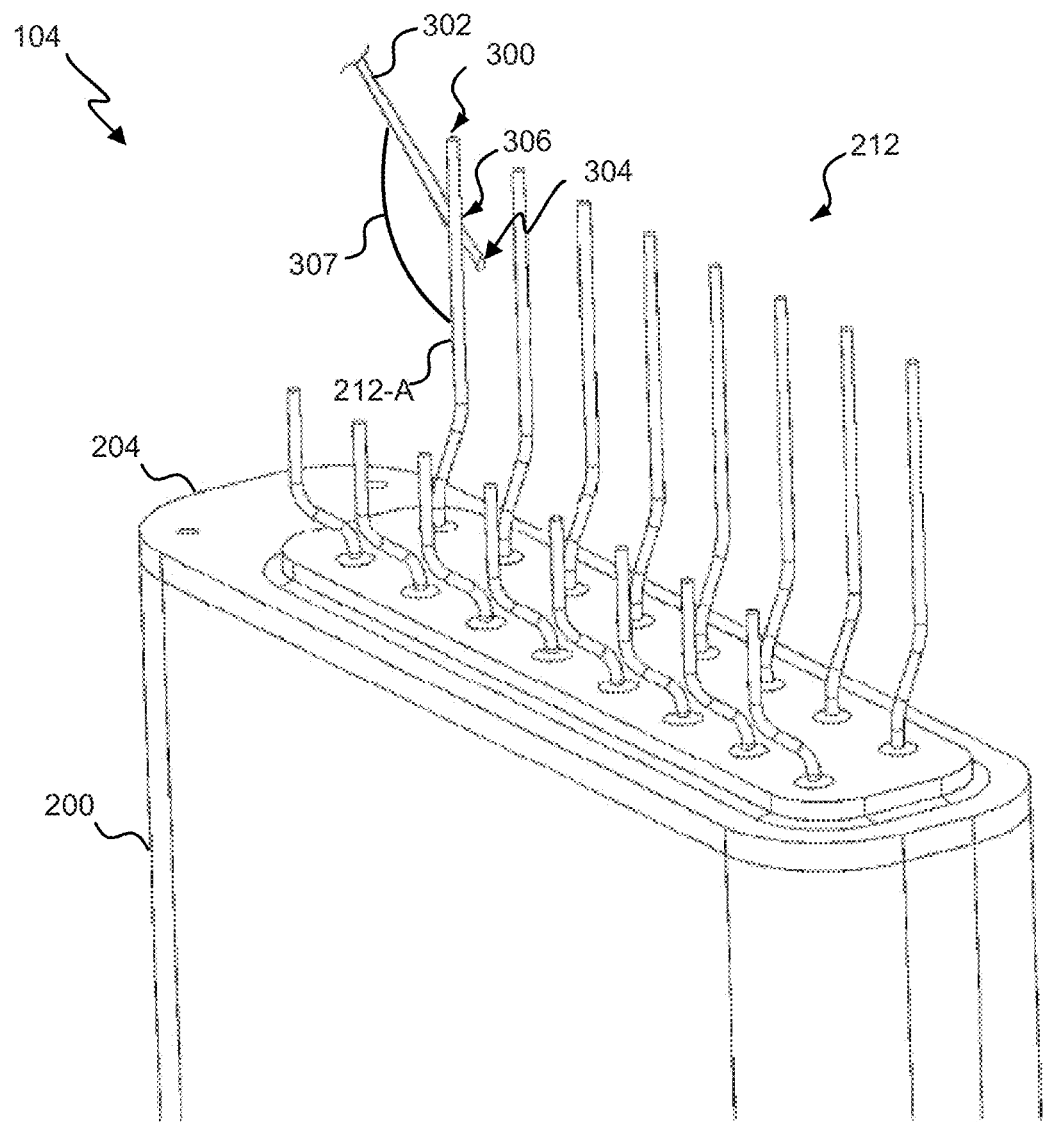
FIG. 4 is a perspective view of one embodiment of portions of the implantable pulse generator.
Figure 5:
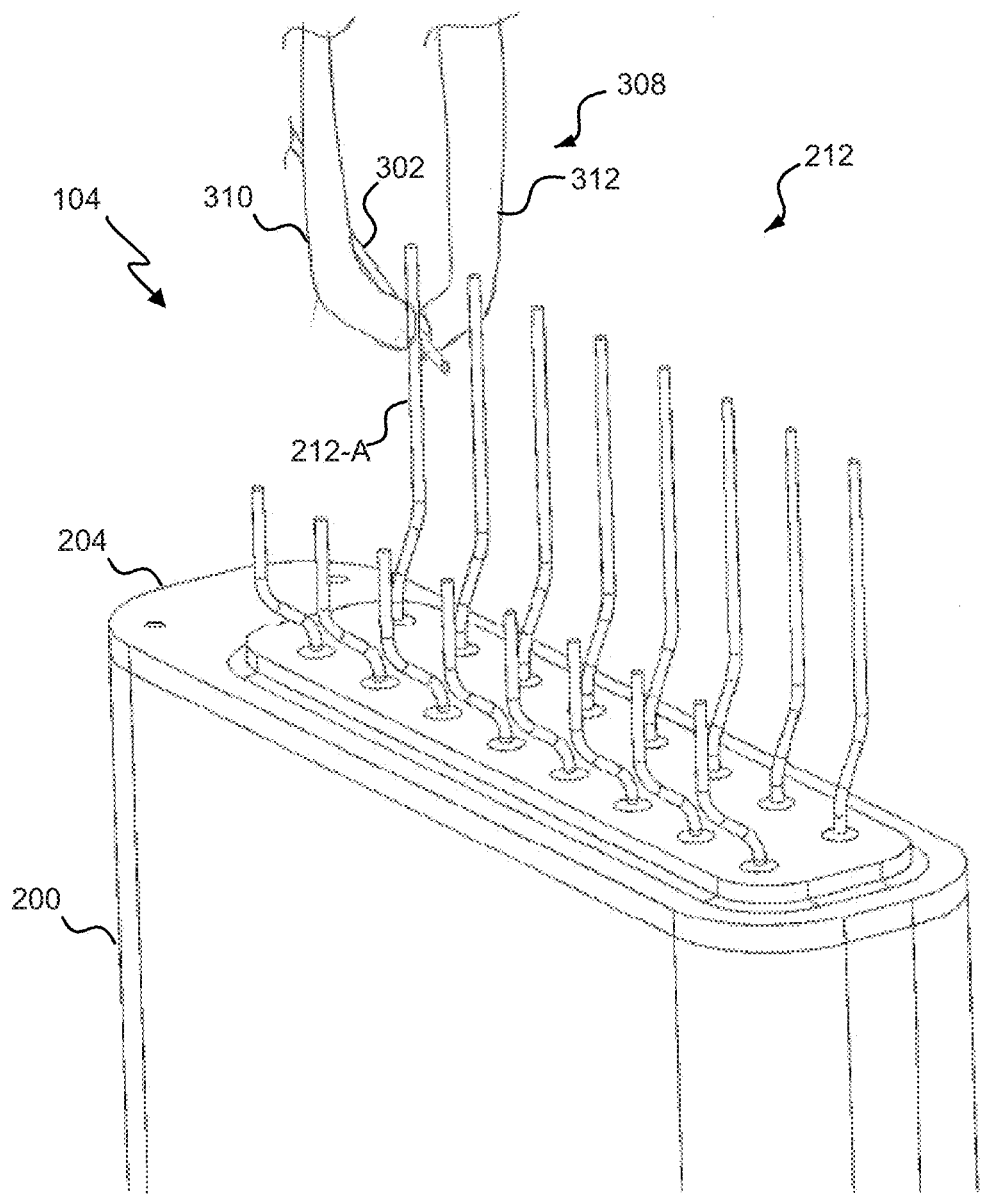
FIG. 5 is a perspective view of one embodiment of portions of the implantable pulse generator and a welder.
Figure 6:
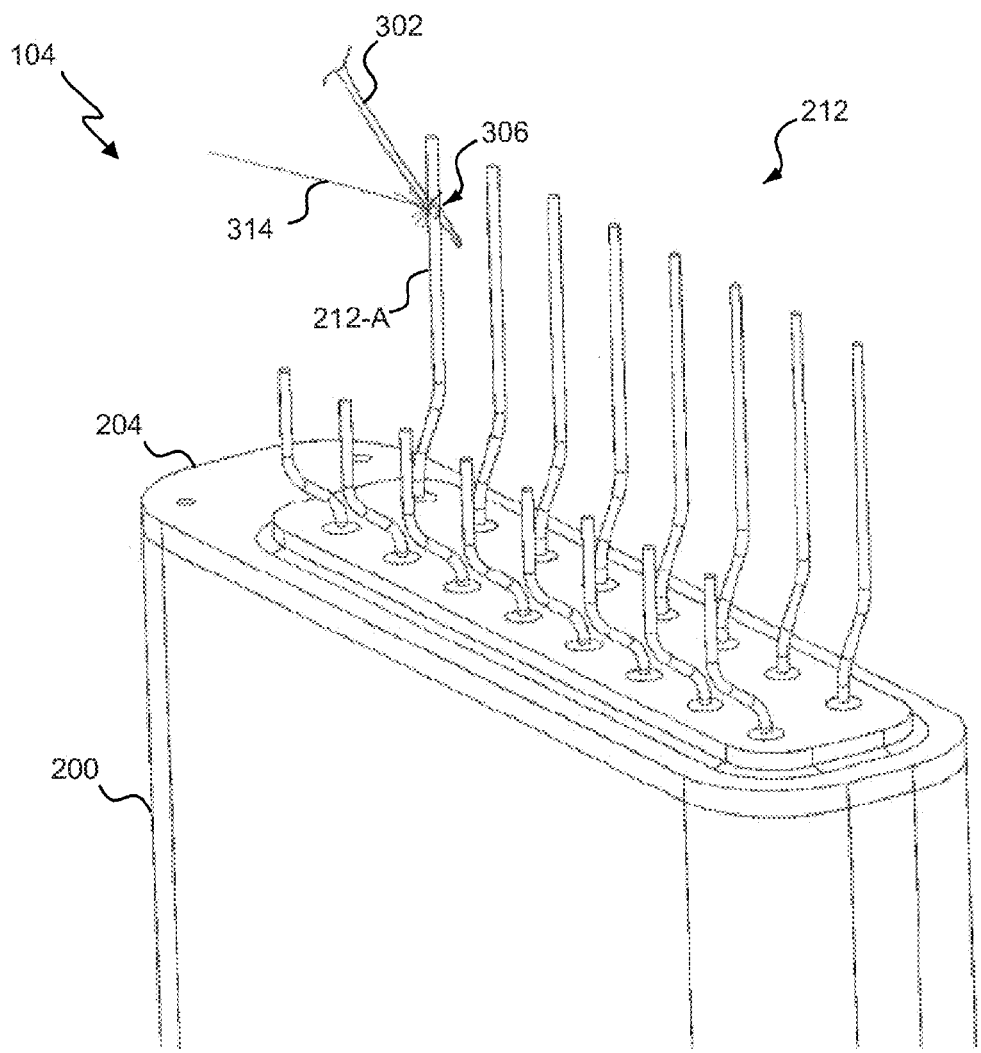
FIG. 6 is a perspective view of one embodiment of portions of the implantable pulse generator during an energy welding process.

FIGS. 4-6 illustrate one embodiment of a process for connecting wires 212 of the implantable pulse generator 104 to one or several second wires. In some embodiments, the process depicted in FIGS. 4-6 can be performed when it is desired to permanently attach leads 106, 108 or a connecting wire 114 to the implantable pulse generator 104.

FIG. 4 depicts a perspective view of one embodiment of portions of the implantable pulse generator 104. The implantable pulse generator 104 includes the body 200, the feedthrough plate 204, and the plurality of wires 212. In FIG. 4, a first wire 212-A is depicted, which first wire 212-A includes an end 300. The process begins, as depicted in FIG. 4, when a second wire 302 is positioned so as to overlap a portion of the first wire 212-A. The second wire 302 can comprise a variety of shapes and sizes and can be made from a variety of materials. In some embodiments, the second wire 302 can have the same properties and/or be made of the same materials as the wires 212 including, for example, the first wire 212-A. Thus, in one embodiment, the second wire 302 can be biocompatible and can be cylindrically shaped.

The second wire 302 can be positioned such that an end 304 of the second wire 302 extends across the first wire 212-A to create a junction 306, joint, or overlapping portion. In some embodiments, the longitudinal axes of the first wire 212-A and the second wire 302 at the junction 306 can be nonparallel such that an angle 307 between the longitudinal axis of the first wire 212-A and the longitudinal axis of the second wire 302 is not 180°. In some embodiments, the angle 307 between the longitudinal axis of the first wire 212-A and the longitudinal axis of the second wire 302 can be, for example, between 20° and 160°, between 30° and 150°, between 45° and 135°, between 60° and 120°, between 80° and 100°, approximately 25°, approximately 30°, approximately 45°, approximately 60°, approximately 90°, approximately 120°, approximately 150°, and/or any other or intermediate value.

After the second wire 302 has been positioned with respect to the first wire 212-A such that a junction 306 or overlapping portion is created, the process proceeds to FIG. 5 wherein the second wire 302 is connected to the first wire 212-A via a first, resistance weld. In some embodiments, and as depicted in FIG. 5, the resistance weld (first weld) is created by a resistance welder 308. In some embodiments, the resistance weld can be configured to pass an electric current to the junction 306 or overlapping portion of the first and second wires 212-A, 302. In some embodiments, the resistance welder 308 can comprise a first electrode 310 and a second electrode 312. In some embodiments, the first electrode 310 and the second electrode 312 are each configured to contact one of the first and second wires 212-A, 302. In some embodiments, the first and second electrodes 310, 312 are each further configured to apply a force to one of the first and second wires 212-A, 302 to achieve the desired contact force between the first and second wires 212-A, 302.

The first and second electrodes 310, 312 can comprise a variety of shapes and sizes. In some embodiments, the first and second electrodes 310, 312 can be sized and shaped so as to allow welding of a single one of the wires 212 at a time, and in some embodiments, the first and second electrodes 310, 312 can be size and shaped so as to allow welding of a plurality of the wires 212 at a time. In some embodiments, the contacting faces of the first and second electrodes 310, 312 that contact the first and second wires 212-A, 302 can have a dimension (e.g. width or diameter) that is, for example, of 1 time, 2 times, 3 times, 4 times, 5 times, 10 times, 20 times, 40 times, or any other or intermediate factor larger than the diameter of one or both of the wires 212-A, 302. In some embodiments, this dimension can be, for example, 0.2 mm, 0.5 mm, 1 mm, 2 mm, 4 mm, or any other or intermediate dimension.

The resistance welder 308 can be configured to pass a desired current from the first electrode 210 to one of the first and second wires 212-A, 302, from one of the first and second wires 212-A, 302 to the other of the first and second wires 212-A, 302, and from the other of the first and second wires 212-A, 302 to the second electrode 312. In some embodiments, the points of physical contact between one of the electrodes 310, 312 and one of the wires 212-A, 302 or between both of the wires 212-A, 302 are interfaces. In some embodiments, the resistance weld is formed at the interface having the highest resistance. To ensure that the interface having the highest resistance is the interface at which the wires 212-A, 302 contact each other, in some embodiments, the contacting faces of the electrodes 310, 312, which contacting faces are the portions of the electrodes 310, 312 that contact one of the wires 212-A, 302, can be configured for low resistance. In some embodiments, the contacting faces can be, for example, polished to allow a low resistance contact between the contacting faces and the wires 212-A, 302.

As seen in FIG. 5, in some embodiments, the first and second electrodes 310, 312 can be positioned so as to be on opposite sides of the junction 306 of the first and second wires 212-A, 302. Advantageously, this positioning can facilitate the creation of forces necessary to achieve the desired resistance weld. After the first and second electrodes 310, 312 are positioned, the first and second electrodes 310, 312 can be brought into contact with the wires 212-A, 302 the desired force can be generated by the first and second electrodes 310, 312, the desired current can be passed from the first electrode 310 to the second electrode 312, and the first and second electrodes 310, 312 can be removed from the wires 212-A, 302.

After the first and second electrodes 310, 312 have been removed from the first and second wires 212-A, 302, the process may proceed as depicted in FIG. 6, wherein the first and second wires 212-A, 302 are energy beam welded together. In some embodiments, for example, the resistance welding of the first and second wires 212-A, 302 can connect the first and second wires 212-A, 302, but it can be difficult to evaluate the quality of that resistance weld. In some embodiments, while energy beam welding allow simple evaluation of the quality of the resulting weld, the size of the first and second wires 212-A, 302 can make it difficult to adequately hold the first and second wires 212-A, 302 to allow energy beam welding. Advantageously, the combination of these welding techniques results in a synergistic benefit of easily fixing the position of the first and second wires 212-A, 302 and achieving a weld which can be easily evaluated. In some embodiments, for example, energy beam welding can create a weld bead when that is visible to the human eye when the weld is successful. Thus, the weld can be visually evaluated without using any equipment.

In some embodiments, the energy beam 314 of an energy beam welder including, for example, the laser beam of a laser welder, can be aimed at or is otherwise directed at some or all of the junction 306 of the first and second wires 212-A, 302. This energy beam 314 can include a centerline axis. In some embodiments, the energy beam 314 of the energy beam welder can be directed at the first resistance weld created according to the steps of FIG. 5, and in some embodiments, the energy beam 314 of the energy beam welder can be offset from the resistance weld created according to the steps of FIG. 5. In some embodiments, the energy beam 314 can be directed at a location that is, for example, separated from the resistance weld (first weld) by 0.01 mm, 0.05 mm, 0.1 mm, 0.12 mm, 0.2 mm, 0.3 mm, 0.5 mm, 0.6 mm, 0.8 mm, 1 mm, to millimeters, 3 mm, 5 mm, or any other or intermediate distance.

In some embodiments, the energy beam 314 can be positioned to improve the energy beam weld (second weld). In some embodiments, this positioning can be such that the energy beam 314 does not sever one or both of the first and second wires 212-A, 302. In some embodiments, one or both of the first and second wires 212-A, 302 can be severed if the energy beam 314 is aimed at a portion of one or both of the first and second wires 212-A, 302 other than the ends 300, 304 of one or both of the first and second wires 212-A, 302 and if the power delivered by the energy beam 314 to that portion of one or both of the first and second wires 212-A, 302 melts all of the material in a cross-section of one or both of the first and second wires 212-A, 302 at that portion.

In some embodiments, the severing of one or both of the first and second wires 212-A, 302 can be prevented by aiming the energy beam 314 at one or both of the ends 300, 304 of the first and second wires 212-A, 302. In some embodiments, the severing of one or both of the first and second wires 212-A, 302 can be prevented by aiming the energy beam 314 such that the energy beam 314 does not melt all of the material in the cross-section of the portion of the one or both of the first and second wires 212-A, 302 at which the energy beam 314 is aimed. In some embodiments, this can be achieved by aiming the energy beam 314 such that the centerline axis of the energy beam 314 is offset from one or both of the longitudinal axes of the first and second wires 212-A, 302. Alternatively, in some embodiments, the energy beam 314 can be aimed such that only a portion of the energy beam 314 impinges on one or both of first and second wires 212-A, 302. In some embodiments, the energy beam 314 can be aimed such that a portion of the energy beam 314, including, for example, the centerline axis of the energy beam 314 is tangent or approximately tangent with some of the portions of the first and/or second wires 212-A, 302 on which the energy beam 314 impinges, and in some embodiments, this can include aiming the energy beam 314 such that the energy beam does not impinge on half of the perimeter of a portion of one or both of the first and second wires 212-A, 302, and/or does not impinge on the entire width of a portion of one or both of the first and second wires 212-A, 302. In some embodiments, the aiming of the energy beam 314 can include prepositioning the energy beam 314 and moving and/or positioning the implantable pulse generator 104 to a desired position, such as, for example, placing the implantable pulse generator into a jig or fixture having a desired orientation and position with respect to the energy beam 314.

Figure 6A:
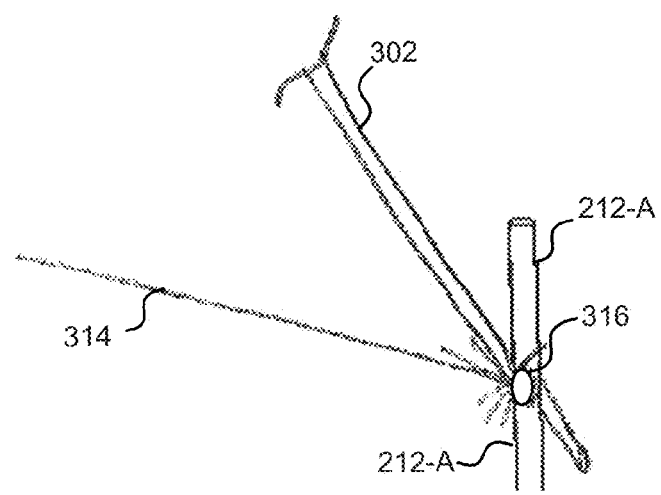
FIG. 6A is a perspective view of one embodiment of an energy beam contacting a peripheral edge of a wire.

After the energy beam 314 has been aimed, the energy beam 314 can be activated and the second, energy beam weld can be completed. In some embodiments, and as depicted in FIG. 6A, the energy beam 314 can contact a peripheral edge of one or both of the first and second wires 212-A, 302 and can generate a fusion zone 316 and/or a heat affected zone that extends from the point of contact of the energy beam 314 with the peripheral edge of one or both of the first and second wires 212-A, 302. In some embodiments, the fusion zone 316 can be the welded portions of the first and second wires 212-A, 302. In some embodiments, the fusion zone 316 and/or the heat affected zone can extend from the point of contact of the energy beam 314 with the peripheral edge of one or both of the first and second wires 212-A, 302 to the opposing peripheral edge of one or both of the first and second wires 212-A, 302, and in some embodiments, the fusion zone 316 and/or the heat affected zone can partially extend from the point of contact of the energy beam 314 with the peripheral edge of one or both of the first and second wires 212-A, 302 to the opposing peripheral edge of one or both of the first and second wires 212-A, 302.

After the first and second wires 212-A, 302 have been welded, the energy beam 314 may be deactivated and the energy beam weld (second weld) can cool. In some embodiments, this process can be repeated until a desired number of second wires 302 have been connected to the wires 212 of the implantable pulse generator 104. After the desired number of second wires 302 have been connected to the wires 212 of the implantable pulse generator 104, the cap 202 can be formed around or positioned over the wires 212, and specifically around the junction 306 of the wires 212 and the second wires 302. In some embodiments, the cap 202 can be formed of a reactive, biocompatible resin such as, for example, epoxy.

Figure 7:
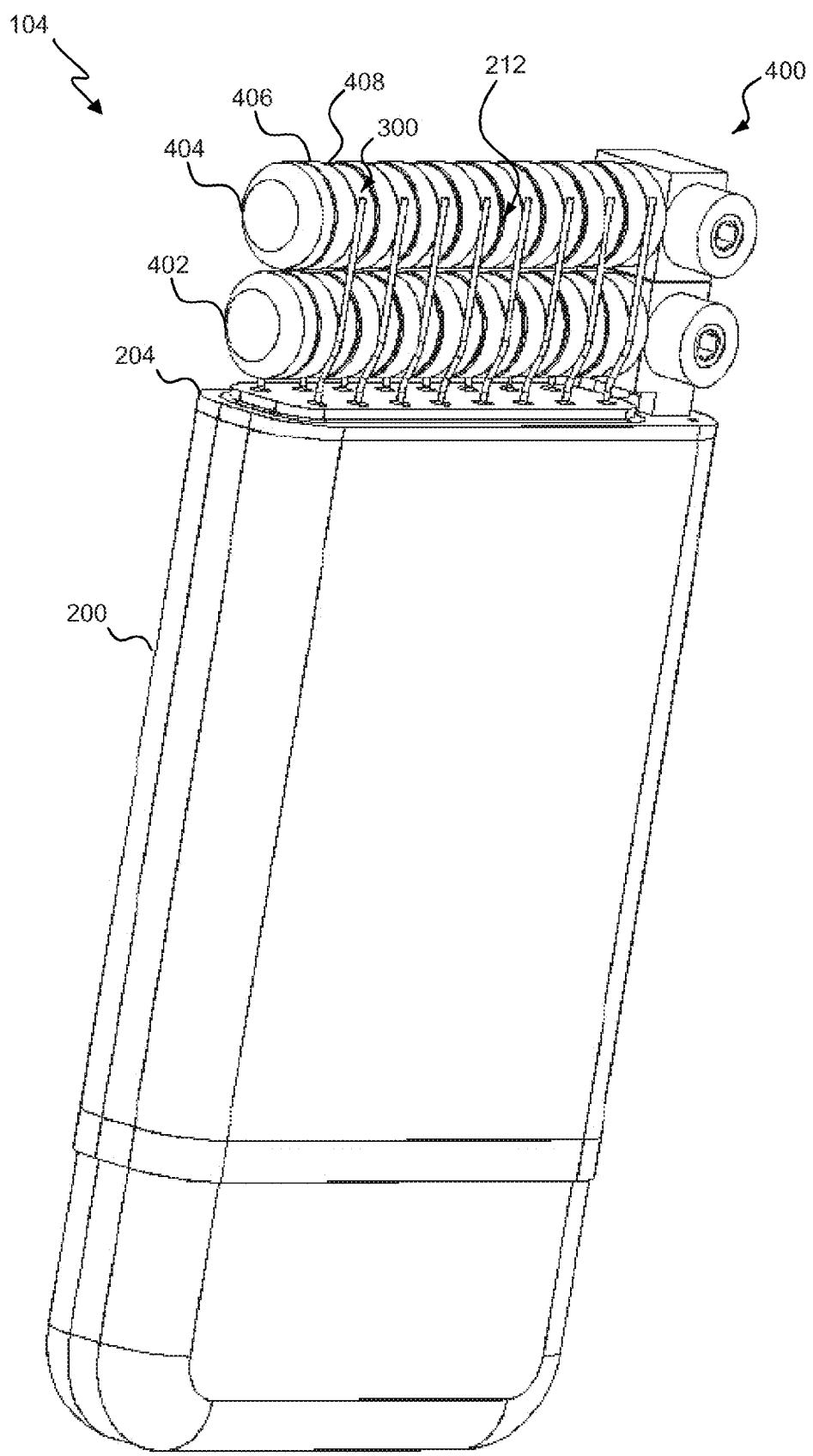
FIG. 7 is perspective view of one embodiment of the connection wires and the connector stack of the implantable pulse generator.

With reference now to FIG. 7, a perspective view of one embodiment of the connection wires 212 and a connector stack 400 of the implantable pulse generator 104 is shown. In some embodiments, the connector stack 400 can be mounted on top of the feedthrough plate 204. The connector stack 400 can include one or several connectors that can connect to some or all of the wires 212 of the implantable pulse generator 104. In some embodiments, the connectors and/or the connector stack can include the connector receptacle 206 shown in FIG. 2. Advantageously, the connector stack 400 can allow the detachable connection of the leads 106, 108 or the connector cable 114 to the implantable pulse generator 104.

The connector stack can, in some embodiments, include a first connector 402 and the second connector 404. In some embodiments, the first connector 402 can be configured to connect to a first group of the wires 212, and the second connector 404 can be configured to connect to a second group of the wires 212. The connectors 402, 404 can comprise a variety of shapes, sizes, and/or connector types. In some embodiments, the connectors 402, 404 can be sized and shaped to allow encapsulation within the cap 202 without extending beyond the perimeter of the body 200 and the feedthrough plate 204.

The connectors 402, 404 can comprise a plurality of conductor contacts 406 and/or insulators 408. In some embodiments, the conductor contacts 406 comprise a plurality of rings made of a conductive material and extending around the periphery of portions of the connectors 402, 406 and the insulators 408 comprise a plurality of rings made of an insulating material and extending around the periphery of portions of the connectors 402, 406. In some embodiments, the conductor contacts 406 and the insulators 408 can be positioned in an alternating manner so that each of the conductor contacts 406 are adjacent to some of the insulators 408 and each of the insulators 408 are adjacent to some of the conductor contacts 406. In some embodiments, one of the wires 212 can be connected to one of the conductor contacts 406.

Figure 8:
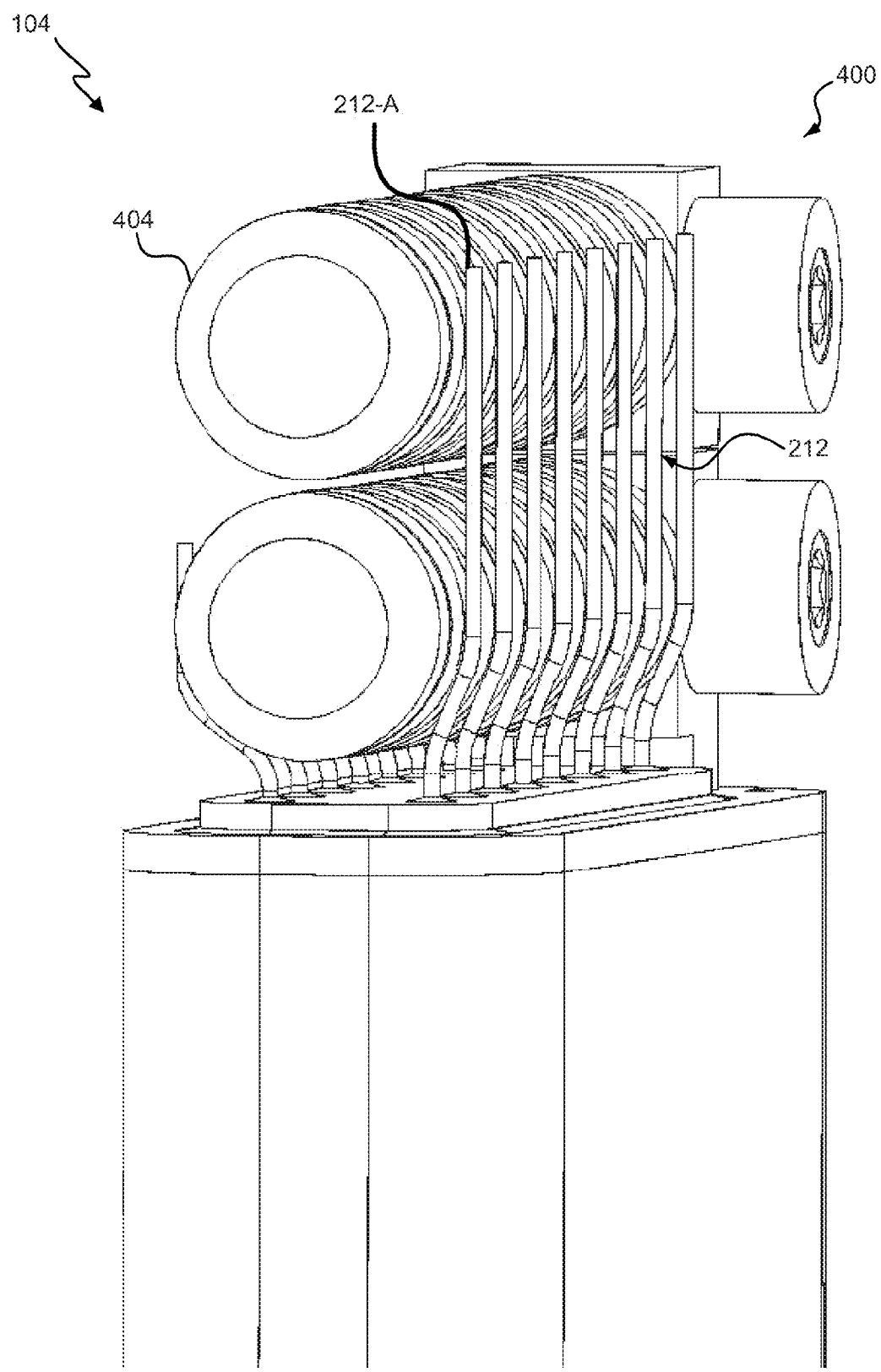
FIG. 8 is a close-up perspective view of one embodiment of the connection wires and the connector stack of the implantable pulse generator.
Figure 9:
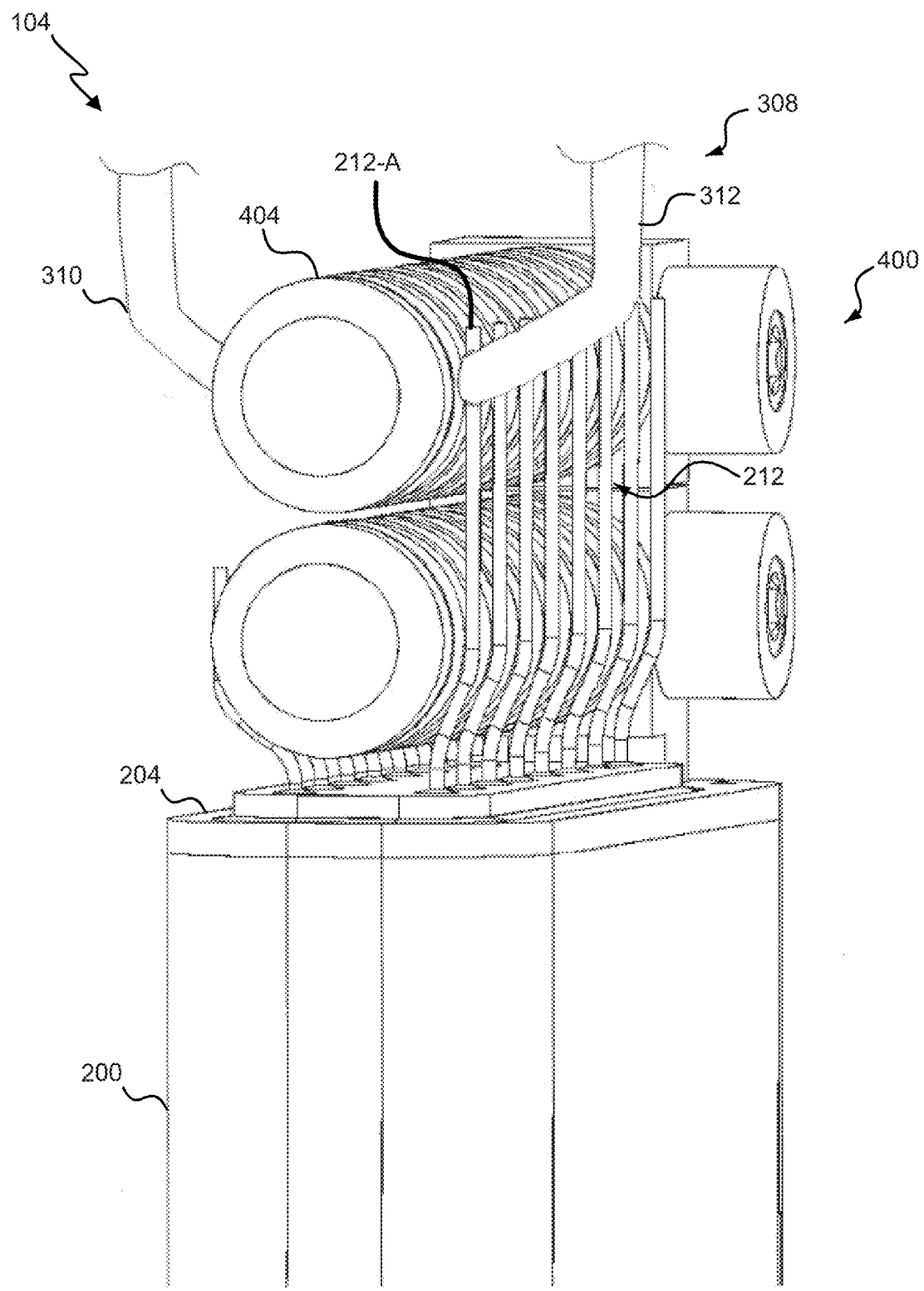
FIG. 9 is a close-up perspective view of one embodiment of the connection wires being resistance welded to the connector stack of the implantable pulse generator.
Figure 10:
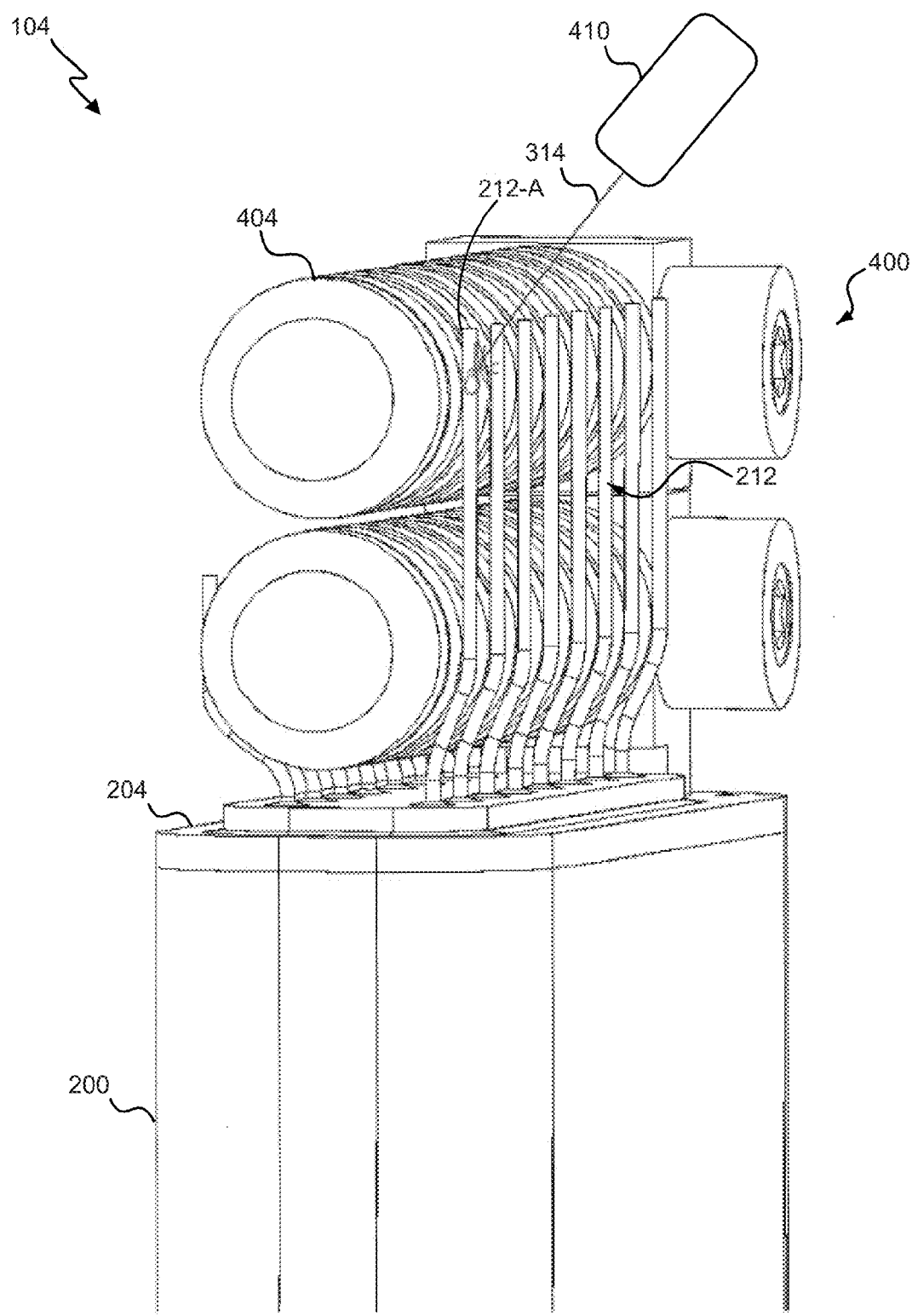
FIG. 10 is a close-up perspective view of one embodiment of the connection wires being energy beam welded to the connector stack of the implantable pulse generator.

With reference now to FIGS. 8-10 one embodiment of a process for connecting one or more of the connection wires 212 of the implantable pulse generator 104 to one of the connectors 402, 404 is shown. Specifically, FIGS. 8-10 depicts one embodiment of a process for connecting one or more of the connection wires 212 of the implantable pulse generator 104 to one of the conductor contacts 406 of the second connector 404. The process starts in FIG. 8, wherein the first wire 212-A is positioned in proximity to the desired one of the conductor contacts 406 and/or is positioned in contact with the desired one of the conductor contacts 406. The first wire 212-A can be positioned such that an end 300 of the first wire 212-A extends across a portion of the second connector 404 to create a junction, joint, or overlapping portion.

In some embodiments, the above discussed positioning of the first wire 212-A can result in undesirable positioning of the first wire 212-A proximate or in contact with a portion of the first connector 402 including, for example, one of the conductor contacts 406 of the first connector 402. In some embodiments, the portion of the first wire 212-A positioned proximate to or in contact with the portion of the first connector 402 can be separated from the first connector 402 via an insulative piece. In some embodiments, the insulative piece can be made of an insulating material and can prevent undesired electrical contact between the first connector 402 and the first wire 212-A. In some embodiments, the insulative piece can be formed on the first wire 212-A, and in one embodiment, the insulative piece can comprise a reactive resin coating of the portion of the first wire 212-A that is positioned proximate to or in contact with the first connector 402. In some embodiments, the reactive resin coating of the portion of the first wire 212-A can be the same type of reactive resin coating used in the creation of the cap 202. Advantageously, use of the same reactive resin coating on the portion of the first wire 212-A as is used in the cap 202 can facilitate bonding between the reactive resin coating of the portion of the first wire 212-A and the reactive resin of the cap 202.

After the first wire 212-A has been positioned with respect to the second connector 404 such that a junction or overlapping portion is created, the process proceeds to FIG. 9 wherein the second first wire 212-A is connected to the second connector via a resistance weld (first weld). In some embodiments, and as depicted in FIG. 9, the resistance weld (first weld) can be created by the resistance welder 308. In some embodiments, the resistance welder 308 can be configured to pass an electric current to the junction or overlapping portion of the first wire 212-A and the second connector 404. In some embodiments, the resistance welder 308 can comprise a first electrode 310 and a second electrode 312 that can each be configured to contact one of the first wire 212-A and the desired conductor contact 406 of the second connector 404. The first and second electrodes 310, 312 can include all of the properties and attributes, and perform all of the functions discussed above with respect to FIGS. 4-6.

After the resistance weld (first weld) has been created between the first wire 212-A and the second connector 404, the process proceeds as depicted in FIG. 10, wherein the first wire 212-A and the desired one of the conductor contacts 406 of the second connector 404 are energy beam welded together. In some embodiments, this can be performed by the aiming of the energy beam 314, which originates at an energy beam welder 410 that can be, for example, a laser welder, at the desired location on the first wire 212-A, and specifically at the desired location on the junction between the first wire 212-A and the second connector 404. In some embodiments, the energy beam 314 can be aimed as discussed above with respect to FIGS. 4-6 except that the energy beam 314 can be aimed at an edge of the first wire 212-A and at any portion of the appropriate one of the conductor contacts 406 of the second connector 404.

After the energy beam 314 has been aimed, the energy beam 314 can be activated and the energy beam weld (second weld) can be completed. Similar to the discussion with respect to FIG. 6A, the creation of the energy beam weld (second weld) can generate a fusion zone and/or a heat affected zone that extends from the point of contact of the energy beam 314 with the peripheral edge of the first wire 212-A. The fusion zone and/or the heat affected zone can extend from the point of contact of the energy beam 314 with the peripheral edge of the first wire 212-A to the opposing peripheral edge of the first wire 212-A, and in some embodiments, the fusion zone 316 and/or the heat affected zone can partially extend from the point of contact of the energy beam 314 with the peripheral edge of the first wire 212-A to the opposing peripheral edge of the first wire 212-A.

After the energy beam weld (second weld) has been completed, the energy beam welder 410 is deactivated and the energy beam weld (second weld) can cool. In some embodiments, this process can be repeated until all of a desired number of wires 212 have been connected to desired conductive contacts 406 of the first and second connectors 402, 404 of the implantable pulse generator 104. After all of a desired number of wires 212 have been connected to desired conductive contacts 406 of the first and second connectors 402, 404 of the implantable pulse generator 104, the cap 202 can be formed around the wires 212 and the connector stack 400, and specifically around the junction of the wires 212 and the connector stack. In some embodiments, the cap 202 can be formed of a reactive, biocompatible resin such as, for example, epoxy. In some embodiments, after the cap 202 has been completed, the implantable pulse generator 104 can be connected to leads 106, 108 and implanted in a patient.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of connecting leads to an implantable pulse generator, wherein the implantable pulse generator comprises: a biocompatible housing; a plurality of biocompatible wires extending from the biocompatible housing, wherein each of the biocompatible wires comprises a longitudinal axis; and a feedthrough, wherein the feedthrough and the biocompatible housing together define a sealed volume, and wherein the biocompatible wires extend through the feedthrough;
   positioning one of the biocompatible wires and a connecting piece such that the one of the biocompatible wires and the connecting piece contact;
   resistance welding one of the biocompatible wires and the connecting piece together; and
   energy beam welding the one of the biocompatible wires and the connecting piece together.

2. The method of claim 1, wherein the one of the biocompatible wires and the connecting pieces are positioned to create a lap-joint.

3. The method of claim 1, wherein energy beam welding comprises laser welding.

4. The method of claim 1, wherein energy beam welding the biocompatible wire comprises:
   aiming an energy beam at an edge of the one of the biocompatible wires such that a portion of the energy beam is tangent to the edge; and
   welding the edge of the one of the biocompatible wires to the connecting piece.

5. The method of claim 4, wherein the heat affected zone created by welding the edge of the one of the biocompatible wires to the connecting piece extends from the edge of the one of the biocompatible wires.

6. The method of claim 5, wherein the heat affected zone created by welding the edge of the one of the biocompatible wires to the connecting pieces extends to a second edge of the one of the biocompatible wires.

7. The method of claim 1, further comprising enclosing the welds of the one of the biocompatible wires and the connecting piece in a non-conductive material.

8. The method of claim 7, wherein the non-conductive material comprises a reacted resin.

9. The method of claim 1, wherein the connecting piece comprises a second biocompatible wire comprising a longitudinal axis.

10. The method of claim 9, wherein the positioning the one of the biocompatible wires and the connecting piece comprising the second biocompatible wire comprises overlapping a portion of both the one of the biocompatible wires and the second biocompatible wire such that the longitudinal axes of the biocompatible wire and the second biocompatible wire are non-parallel.

11. The method of claim 10, wherein an angle between the longitudinal axes of the biocompatible wire and the second biocompatible wire is between 30 and 150 degrees.

12. The method of claim 1, wherein the connecting piece comprises at least one connector.

13. The method of claim 1, wherein the connecting piece comprises a first connector and a second connector, wherein a first group of the biocompatible wires connect to the first connector and a second group of biocompatible wires extend past the first connector and connect to the second connector.

14. The method of claim 13, further comprising creating an insulative barrier between the second group of wires and the first connector before welding the second group of wires to the second connector.

15. The method of claim 1, wherein resistance welding comprises contacting at least one of the biocompatible wires and the connecting piece with at least one electrode of a resistance welder.

16. The method of claim 1, wherein the wires comprise a diameter between 0.05 mm and 0.5 mm.

17. An implantable pulse generator comprising:
   a biocompatible housing;

a plurality of biocompatible wires extending from the biocompatible housing, wherein each of the biocompatible wires comprises a longitudinal axis;

a feedthrough, wherein the feedthrough and the biocompatible housing together define a sealed volume, and wherein the biocompatible wires extend through the feedthrough;

and a conductive connecting piece welded to one of the biocompatible wires, wherein the conductive connecting piece is joined to one of the biocompatible wires at a joint via a first weld and a second weld, wherein the second weld is offset from the longitudinal axis of the one of the biocompatible wire or at the end of the biocompatible wire.

18. The implantable pulse generator of claim 17, wherein the plurality of biocompatible wires comprise a platinum-iridium alloy.

19. The implantable pulse generator of claim 17, wherein the joint of the one of the biocompatible wires and the conductive connecting piece comprises a lap joint.

20. The implantable pulse generator of claim 17, further comprising a cap enclosing the biocompatible wires and the joint of the one of the biocompatible wires and the connecting piece.

21. The implantable pulse generator of claim 20, wherein the cap is non-conductive.

22. The implantable pulse generator of claim 20, wherein the cap is permeable to body fluids.

23. The implantable pulse generator of claim 20, wherein the cap comprises a reacted resin.

24. The implantable pulse generator of claim 17, wherein the connecting piece comprises a second biocompatible wire having a longitudinal axis.

25. The implantable pulse generator of claim 24, wherein at the first weld of the joint, the longitudinal axis of the one of the biocompatible wires is non-parallel with the longitudinal axis of the second biocompatible wire.

26. The implantable pulse generator of claim 17, wherein the connecting piece comprises at least one connector.

27. The implantable pulse generator of claim 17, wherein the connecting piece comprises a first connector and a second connector, wherein a first group of the biocompatible wires connect to the first connector and a second group of biocompatible wires extend past the first connector and connect to the second connector.

28. A method of connecting leads to an implantable pulse generator, wherein the implantable pulse generator comprises: a biocompatible housing; an array of biocompatible wires extending from the biocompatible housing, wherein each of the biocompatible wires comprises a longitudinal axis; and a feedthrough, wherein the feedthrough and the biocompatible housing together define a sealed volume, and wherein the biocompatible wires extend through the feedthrough;

resistance welding each of the biocompatible wires of the array of biocompatible wires to a connecting piece; and energy beam welding each of the biocompatible wires of the array of biocompatible wires to the connecting piece.

29. The method of claim 28, wherein the connecting piece comprises a plurality of second wires, and wherein each of the biocompatible wires of the array of biocompatible wires is connected to a unique one of the second wires.

30. The method of claim 28, wherein the connecting piece comprises a connector having a plurality of contacts, and wherein each of the biocompatible wires of the array of biocompatible wires is connected to a unique one of the plurality of contacts.

31. The method of claim 28, wherein resistance welding comprises contacting at least one of the biocompatible wires and connecting piece with at least one electrode of a resistance welder.

32. The method of claim 28, wherein the wires comprise a diameter between 0.05 mm and 0.5 mm.

* * * * *